(12) United States Patent
Saeedi et al.

(10) Patent No.: US 10,737,137 B2
(45) Date of Patent: Aug. 11, 2020

(54) BIOFEEDBACK BELT SYSTEM

(71) Applicants: Alireza Saeedi, North York (CA); Hamid Izadi, Thornhill (CA)

(72) Inventors: Alireza Saeedi, North York (CA); Hamid Izadi, Thornhill (CA)

(*) Notice: Subject to any disclaimer, the term of this patent is extended or adjusted under 35 U.S.C. 154(b) by 93 days.

(21) Appl. No.: 15/018,460

(22) Filed: Feb. 8, 2016

(65) Prior Publication Data

US 2017/0225028 A1  Aug. 10, 2017

(51) Int. Cl.
 *A63B 23/02* (2006.01)
 *A41F 9/00* (2006.01)
 *A61B 5/00* (2006.01)
 *A61H 1/00* (2006.01)

(52) U.S. Cl.
 CPC .......... *A63B 23/0244* (2013.01); *A41F 9/002* (2013.01); *A61B 5/4561* (2013.01); *A61B 5/486* (2013.01); *A61B 5/742* (2013.01); *A61B 5/7455* (2013.01); *A61H 1/00* (2013.01); *A61H 2205/083* (2013.01)

(58) Field of Classification Search
 CPC ... A63B 23/0244; A41F 9/002; A61B 5/4561; A61B 5/486; A61B 5/742; A61B 5/7455; A61H 1/00; A61H 2205/083
 See application file for complete search history.

(56) References Cited

U.S. PATENT DOCUMENTS

| | | | |
|---|---|---|---|
| 3,561,434 A * | 2/1971 | Kilbey | A61F 5/24 602/36 |
| 4,191,949 A | 3/1980 | Myers | |
| 4,545,370 A | 10/1985 | Welsh | |
| 5,522,401 A | 6/1996 | Brucker | |
| 5,645,080 A | 7/1997 | Toso | |
| 5,728,027 A * | 3/1998 | Sinaiko | A63B 23/0244 340/573.1 |
| 5,823,913 A | 10/1998 | Aruin | |
| 5,862,526 A * | 1/1999 | Longcor | A41F 9/002 2/247 |
| 7,712,155 B1 * | 5/2010 | Pantoja | A44B 11/008 2/321 |
| 2010/0250587 A1 * | 9/2010 | Schmitz | G11B 27/02 707/769 |
| 2012/0245491 A1 | 9/2012 | Amell | |
| 2013/0207889 A1 * | 8/2013 | Chang | A61B 5/0002 345/156 |
| 2015/0065919 A1 * | 3/2015 | Cuevas | A61B 5/1116 600/587 |

* cited by examiner

*Primary Examiner* — James Yang

(74) *Attorney, Agent, or Firm* — Azadeh Saidi

(57) ABSTRACT

A biofeedback belt system which serves as an alert belt with the ability to decrease stomach size as well as decrease the arch of a user-wearers lower back. The invention is designed for patients who have hyper lordosis conditions. The mechanism of the belt is based on biofeedback. When a user-wearer relaxes their abdominal region, the belt produces vibration or sound and the user-wearer must tighten their abdominal region to discontinue the vibration or noise. Biofeedback belt system can also work in a manner such that when the user-wearer tightens their abdominal region, the belt plays music or favorable vibration separately or together as encouragement. Over a period of time of tightening of the abdominal region on a regular basis, the abdominal region size decreases and abdomen strengthens.

2 Claims, 5 Drawing Sheets

BIOFEEDBACK BELT SYSTEM

BACKGROUND OF THE INVENTION

The following includes information that may be useful in understanding the present invention(s). It is not an admission that any of the information provided herein is prior art, or material, to the presently described or claimed inventions, or that any publication or document that is specifically or implicitly referenced is prior art.

1. FIELD OF THE INVENTION

The present invention relates generally to the field of training devices and more specifically relates to a biofeedback belt system.

2. DESCRIPTION OF RELATED ART

The abdominal muscles are a group of six muscles that wrap around the center of the body from the rib cage to the pelvis. These muscles are important to one's health, as they assist with everything from breathing and walking to supporting proper posture and alignment of the spine. Without healthy abdominal muscles supporting posture, the body cannot function properly. Over time, basic tasks become increasingly difficult. Good posture means sitting or standing with shoulders back, abdominal muscles held in, and head tall. Slouching is considered bad posture. With good posture core muscles are engaged, meaning that they are working at all times. The core includes not just your ab muscles, but also those in one's back, hips, butt and pelvis.

A person with good posture is stronger and less prone to injury than an individual with improper form. Lower back pain will decrease on a daily basis if a person has a strong core and good posture. When a person's spine is stabilized in the way that it is meant to be, they are less likely to feel pain or hurt themselves doing normal daily activities. Posture is greatly affected by the way a person handles their abdominal muscles. Standing straight requires pulling abs in towards the spine and holding them there for extended periods of time. Letting the stomach hang freely often contributes to a sagging, slouchy appearance. This is not desirable. Standing or sitting up straight is a great way to engage ab muscles to exercise the core on a daily basis. A suitable solution is desirable whereby posture is efficiently corrected.

Several attempts have been made to solve the above-mentioned problems such as those found in U.S. Pub. No. 2012/0245491 to Fredrik Amell, U.S. Pat. No. 5,823,913 to Alexander S. Aruin; U.S. Pat. No. 5,728,027 to Robert J. Sinaiko; U.S. Pat. No. 4,545,370 to Thomas M. Welsh; U.S. Pat. No. 4,191,949 to Dick T. Myers; U.S. Pat. No. 5,522,401 to Milton Brucker; and U.S. Pat. No. 5,645,080 to Victor Toso. This art is representative of training devices. However, none of the above inventions and patents, taken either singly or in combination, is seen to describe the invention as claimed.

Preferably, a biofeedback belt system should provide user with a means for correcting bad posture and strengthening abdominal muscles and, yet would operate reliably and be manufactured at a modest expense. Thus, a need exists for a reliable biofeedback belt system to avoid the above-mentioned problems.

BRIEF SUMMARY OF THE INVENTION

In view of the foregoing disadvantages inherent in the known training device art, the present invention provides a novel biofeedback belt system. The general purpose of the present invention, which will be described subsequently in greater detail is to alert a user-wearer to enable proper midsection position and proper alignment of a spinal column and correct posture to be promoted.

A biofeedback belt system is disclosed herein, in a preferred embodiment, comprising: a biofeedback belt assembly comprising an adjustable belt having a flexible body (having a front surface, a back surface, a first end, and a second end), at least one fastener and an alarm system (having a means for playing music from a music source, a vibrating means, a processor, a sensor, a memory unit, and a power source). As such, the biofeedback belt system comprises the biofeedback belt assembly. The biofeedback belt assembly comprises the adjustable belt, and the alarm system in functional combination. The flexible body of the adjustable belt is defined by the front surface, the back surface, the first end, and the second end. The back surface is located adjacent to a torso of a user-wearer during use. Relationally speaking, the front surface opposes the back surface.

The first end and the second end of the flexible body are able to be coupled as a continuous waistband to form the adjustable belt via the at least one fastener. The first end and the second end of the flexible body are able to be uncoupled via the at least one fastener for removal of the adjustable belt. The at least one fastener in certain embodiments comprises a ring for tightening and loosening the adjustable belt of the biofeedback belt system. The adjustable belt further may comprise a backpad. The backpad is adjustable relative to the adjustable belt. The backpad preferably comprises flexible material for providing increased comfort to the user-wearer.

The adjustable belt in preferred embodiments comprises flexible material for enabling adjusting the adjustable belt with relative ease. The adjustable belt may comprise measuring marks to indicate a level of tightness of the biofeedback belt system. The alarm system comprises in functional combination the music source, the processor, the sensor, the memory unit, and the power source. The music source may comprise files stored on the memory card. The music source may be used in the form of a portable media player serving as an external data storage device. The biofeedback belt system may further comprise a headphone jack to allow the user-wearer to listen to the music. The sensor, the memory unit, the processor of the alarm system are located within the housing. The alarm system preferably comprises recessed buttons. The alarm system may also comprise a display screen to display alphanumeric indicia. The alarm system further comprises a vibrator in preferred embodiments for alerting the user-wearer as to a posture that is poor.

Referring now to the housing; the housing is structured and arranged to house the sensor, the memory unit, the processor of the alarm system and to protect the sensor, the memory unit, and the processor from damage. The sensor is in proximity to the torso of the user-wearer to sense relative position of the torso such that a proper alignment of a spinal column and the proper the posture is thereby promoted. The sensor is in communication with the processor, and the processor is able to activate the music and alternately the vibrator or both at the same time. The power source provides power for the alarm system. The biofeedback belt system is useful for providing the biofeedback via the sensor to decrease abdomen. Further, the vibration is used to induce as an indication to the user-wearer to change position to decrease an arch of a lower back of the user-wearer such that posture is able to be corrected to the proper posture. Depending on the type of belt (punishment or encouragement type), the music or vibration works in different ways. In 'punishment mode' which is the first and most convenient mode, the music and/or vibration plays when a user fails to maintain proper spine alignment or proper abdominal position. In 'encouragement mode', the music and/or vibration plays the music or vibration as long as the user maintains posture and midsection in proper position. In other embodiments, the belt may compromise both punishment and encouragement types enabled in one housing to let the user choose according to preference. In preferred embodiments music plays to indicate positive biofeedback when the user-wearer corrects posture such that health and the proper posture of the user-wearer are promoted. The housing may comprise the digital time recorder on the screen to record each attempt and total attempt time the user is keeping the abdomen in proper position.

A kit is also described herein including: the biofeedback belt assembly, and a set of user instructions.

A method of using a biofeedback belt system is also disclosed herein comprising the steps of: donning a biofeedback belt assembly to a torso of a user-wearer, adjusting the adjustable belt of the biofeedback belt assembly, and wearing the biofeedback belt assembly to indicate of and promote a proper posture (also indicated is when user-wearer is in a poor posture for correction). The method may further comprise the step of removing the biofeedback belt assembly from the torso of the user-wearer.

The present invention holds significant improvements and serves as a biofeedback belt system. For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, biofeedback belt system, constructed and operative according to the teachings of the present invention.

The various embodiments of the present invention will hereinafter be described in conjunction with the appended drawings, wherein like designations denote like elements.

DETAILED DESCRIPTION

Figure 1:
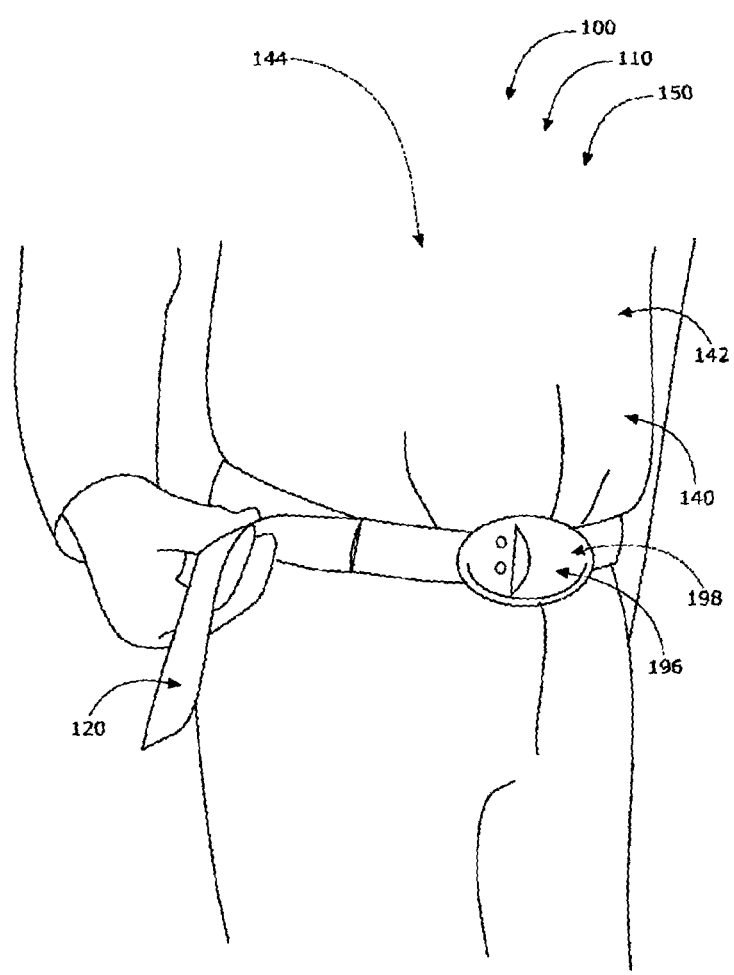
FIG. 1 shows a perspective view illustrating a biofeedback belt system during an 'in-use' condition according to an embodiment of the present invention.
Figure 2:
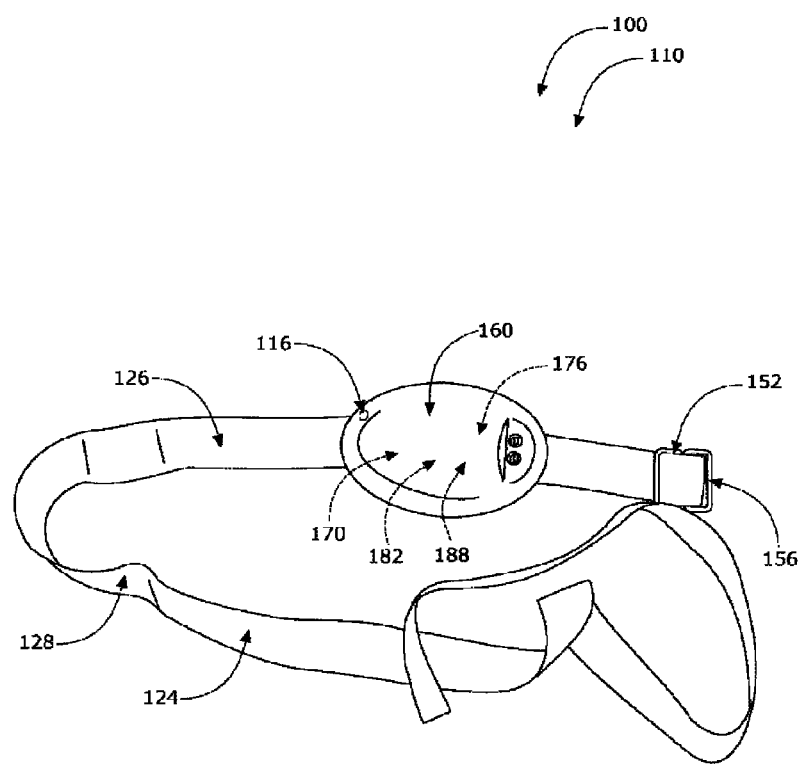
FIG. 2 is a perspective view illustrating a biofeedback belt assembly comprising an alarm system and an adjustable belt according to an embodiment of the present invention of FIG. 1.
Figure 3:
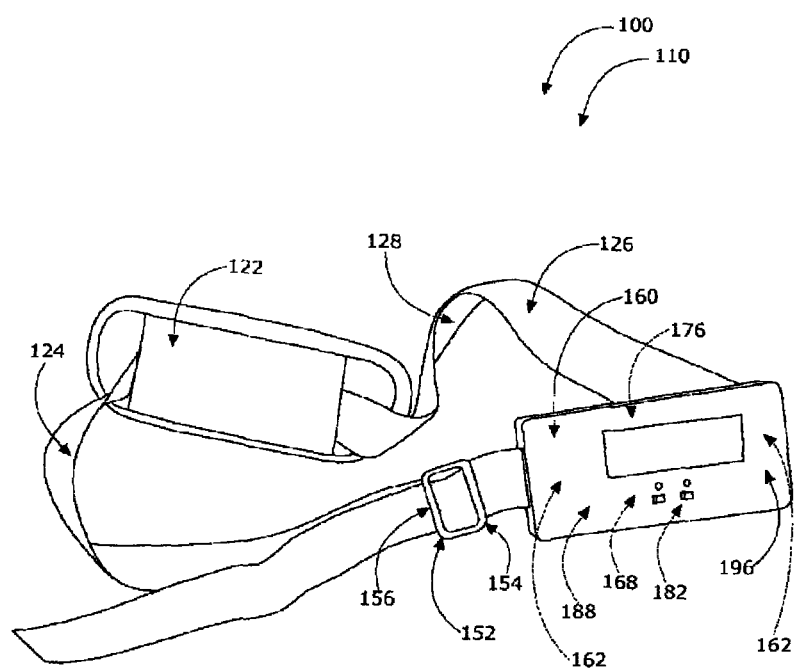
FIG. 3 is a perspective view illustrating various components of the biofeedback belt system according to an embodiment of the present invention of FIGS. 1-2.
Figure 4:
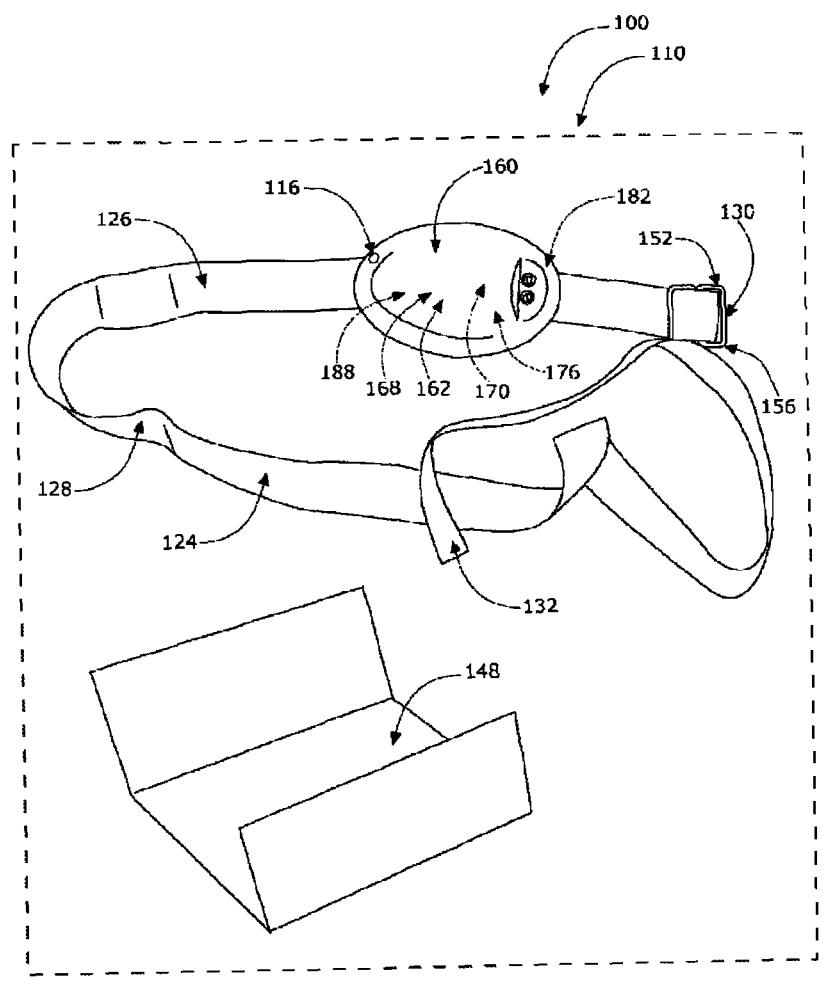
FIG. 4 is a perspective view illustrating various components of the biofeedback belt system as a kit according to an embodiment of the present invention of FIGS. 1-3.

As discussed above, embodiments of the present invention relate to a training device and more particularly to a biofeedback belt system as used to improve a user-wearers attention to posture and abdominal activity.

Generally speaking, the biofeedback belt system is an alert belt with the capability to decrease midsection size as well as decrease an arch of a user-wearers lower back. The invention is designed for patients who have hyper lordosis conditions and also for people who do not have proper midsection size. The mechanisms of the belt are designed to provide biofeedback. There are two mechanisms: first, when a user-wearer relaxes their abdominal region, the belt produces vibration or sound and the user-wearer must tighten their abdominal region to discontinue the vibration or sound. Secondly, when the user-wearer tightens their abdominal region, the belt will play music (as a psuedo-reward).

The belt comprises a headphone jack in certain embodiments whereby headphones can be plugged in to encourage the user-wearer to keep the abdominal region tightened. Other sound producing means may be used. Over a period of time of tightening of the abdominal region on a regular basis, the abdominal region size decreases and abdomen strengthens as a result. The present invention is designed to allow for the degree of tightness to be determined by the users according to personal preference. If a user-wearer fastens the belt too tight, the user must keep the abdominal region pushing relative to the tightness of the belt. Music and vibration (separately or together) are the main feedback means.

Referring now to the drawings by numerals of reference there is shown in FIGS. 1-4, various views of biofeedback belt system 100 comprising: biofeedback belt assembly 110 comprising adjustable belt 120 having flexible body 124 (having front surface 126, back surface 128, first end 130, and second end 132). Adjustable belt 120 further comprises at least one fastener 152, and alarm system 160 (having music source 168, processor 170, sensor 176, memory unit 182, and power source 188). Biofeedback belt system 100 as such comprises biofeedback belt assembly 110.

Biofeedback belt assembly 110 comprises adjustable belt 120 and alarm system 100 in functional combination. Flexible body 124 of adjustable belt 120 is defined by front surface 126, back surface 128, first end 130, and second end 132. First end 130, and second end 132 of flexible body 124 are able to be coupled as a continuous waistband to form adjustable belt 120 via at least one fastener 152, as shown in FIG. 1. First end 130, and second end 132 of flexible body 124 are able to be uncoupled via at least one fastener 152 for removal of adjustable belt 120. Alarm system 160 comprises in functional combination music source 168, processor 170, sensor 176, memory unit 182, and power source 188. Back surface 128 is located adjacent to torso 142 of user-wearer 140 during use, as also shown in FIG. 1. Front surface 126 opposes back surface 128.

Sensor 176, memory unit 182, processor 170 of alarm system 160 is located within housing 196. Housing 196 is structured and arranged to enclose sensor 176, memory unit 182, processor 170 of alarm system 160 to protect sensor 176, memory unit 182, said processor 170 from impact damage. Sensor 176 is in proximity to torso 142 of user-wearer 140 to sense relative position of torso 142 such that a proper alignment of spinal column 144 and posture is promoted. Power source 188 provides power for alarm system 160. Various powering means may be used such as batteries or the like. Biofeedback belt system 100 is useful for providing biofeedback via sensor 176 to decrease abdomen and stomach size (not the organ itself, but referring to the waist) as well as increase an arch of a lower back of user-wearer 140 by inducing a vibration to indicate to user-wearer 140 of a poor posture such that posture is able to be corrected. Music source 168 when played indicates positive biofeedback when user-wearer 140 corrects posture such that health and posture of user-wearer 140 is promoted. In this way the present invention serves as a reward based system for promoting conditioning muscle (and skeletal) memory.

Adjustable belt 120 further comprises backpad 122. Backpad 122 comprises flexible material for providing increased comfort to user-wearer 140. Music source 168 comprises files stored on memory unit 182. Music source 168 preferably comprises wireless communication means using short-wavelength UHF radio waves in an ISM band from 2.4 to 2.485 GHz (such as used by BLUETOOTH). Music source 168 may comprise portable media player 198 serving as an external data storage device. Adjustable belt 120 preferably comprises measuring marks to indicate a relative level of tightness of adjustable belt 120 of biofeedback belt system 100.

Referring to the at least one fastener 152; at least one fastener 152 may comprise hook and loop fasteners 154. At least one fastener 152 may alternately comprises ring 156 for tightening and loosening biofeedback belt system 110. Those with ordinary skill in the art will now appreciate that upon reading this specification and by their understanding the art of indicator means as described herein, methods of use of BLUETOOTH® technology or other suitable equivalents for use in providing music as an indicator of a condition, vibrator means or the like will be understood by those knowledgeable in such art.

Alarm system 160 may comprise recessed buttons. Adjustable belt 120 comprises flexible material in preferred embodiments for enabling ease of adjusting adjustable belt 120. Alarm system 160 comprises vibrator (which may have ability to increase or decrease the intensity of vibration) 162 for alerting user-wearer 140 as to a poor posture and providing massaging of abdominal muscles. Abdominal muscles are caused to be exercised when user-wearer 140 is alerted and corrects their posture. Biofeedback belt system 100 comprises headphone jack 116 to allow user-wearer 140 to listen to music through headphones (speakers may be used). Backpad 122 is adjustable relative to adjustable belt 120. Alarm system 160 comprises a display screen to display indicia.

Biofeedback belt system 100 may be sold as kit 440 comprising the following parts: at least one biofeedback belt assembly 110; and at least one set of user instructions. The kit has instructions such that functional relationships are detailed in relation to the structure of the invention (such that the invention can be used, maintained, or the like in a preferred manner). Biofeedback belt system 100 may be manufactured and provided for sale in a wide variety of sizes and shapes for a wide assortment of applications. Upon reading this specification, it should be appreciated that, under appropriate circumstances, considering such issues as design preference, user preferences, marketing preferences, cost, structural requirements, available materials, technological advances, etc., other kit contents or arrangements such as, for example, including more or less components, customized parts, different indicator combinations, parts may be sold separately, etc., may be sufficient.

Figure 5:
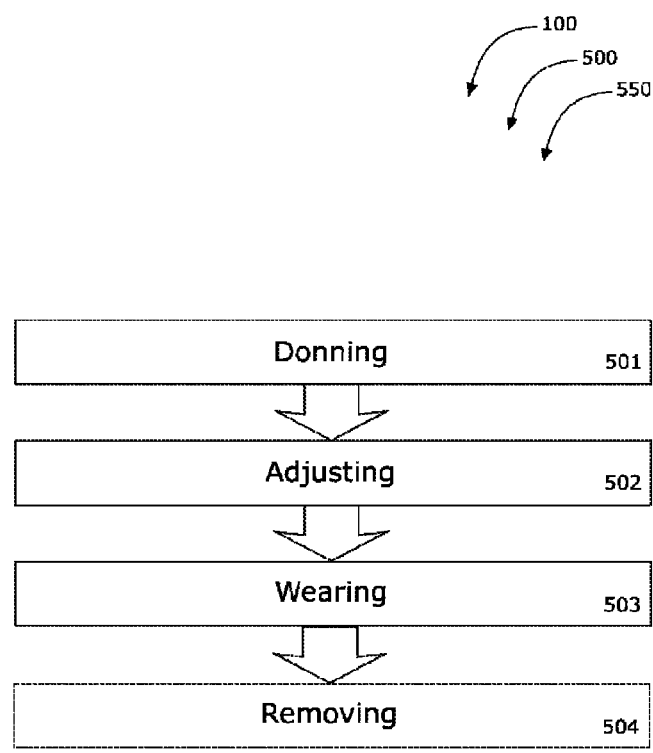
FIG. 5 is a flowchart illustrating a method of use for the biofeedback belt system according to an embodiment of the present invention of FIGS. 1-4.

Referring now to FIG. 5 showing flowchart 550 illustrating method of use 500 for biofeedback belt system 100 according to an embodiment of the present invention of FIGS. 1-4.

As shown, method of use 500 may comprise the steps of: step one 501, donning biofeedback belt assembly 110 to torso 142 of user-wearer 140; step two 502, adjusting biofeedback belt assembly 110; step three 503, wearing biofeedback belt assembly 110 to indicate of and promote proper posture; and step four 504, removing biofeedback belt assembly 110 from torso 142 of user-wearer 140.

It should be noted that step four 504 is an optional step and may not be implemented in all cases. Optional steps of method of use 500 are illustrated using dotted lines in FIG. 5 so as to distinguish them from the other steps of method of use 500.

It should be noted that the steps described in the method of use can be carried out in many different orders according to user preference. The use of "step of" should not be interpreted as "step for", in the claims herein and is not intended to invoke the provisions of 35 U.S.C. § 112, ¶ 6. Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:
1. A biofeedback belt system comprising:
   a biofeedback belt assembly comprising:
   an adjustable belt having:
   a flexible body having:
   a front surface;
   a back surface;
   a first end; and
   a second end;
   at least one fastener; and
   an alarm system having:
   a music playing means and a music source;
   a processor;
   a sensor;
   a memory unit; and
   a power source;
   wherein said biofeedback belt system comprises said biofeedback belt assembly;

wherein said biofeedback belt assembly comprises said adjustable belt, and said alarm system in functional combination;

wherein said flexible body of said adjustable belt is defined by said front surface, said back surface, said first end, and said second end;

wherein said back surface is located adjacent to a torso of a user-wearer during use;

wherein said front surface opposes said back surface;

wherein said first end, and said second end of said flexible body are able to be coupled as a continuous waistband to form said adjustable belt via said at least one fastener;

wherein said first end, and said second end of said flexible body are able to be uncoupled via said at least one fastener for removal of said adjustable belt;

wherein said at least one fastener comprises a ring for tightening and loosening said biofeedback belt system;

wherein said adjustable belt further comprises a backpad;

wherein said backpad is adjustable relative to said adjustable belt;

wherein said backpad comprises flexible material for providing increased comfort to said user-wearer;

wherein said adjustable belt comprises flexible material for enabling adjusting said adjustable belt;

wherein said adjustable belt comprises measuring marks to indicate a level of tightness of said biofeedback belt system;

wherein said alarm system comprises in functional combination said music source, said processor, said sensor, said memory unit, and said power source;

wherein said music source comprises files stored on a memory card;

wherein said music source comprises a portable media player serving as an external data storage device;

wherein said biofeedback belt system comprises a headphone jack to allow said user-wearer to listen to said music;

wherein said sensor, said memory unit, said processor of said alarm system is located within a housing;

wherein said alarm system comprises recessed buttons;

wherein said alarm system comprises a display screen to display alphanumeric indicia;

wherein said alarm system further comprises a vibrator for alerting or encouraging (punishment mode or encouragement mode) said user-wearer as to a posture that is respectfully poor or proper, to help in providing massaging of abdominal muscles and/or playing music that is realized by a proper said posture and; wherein said vibration mechanism, depends on the user's choice (selection of said punishment or encouragement mode), and can be activated as soon as the user fails to maintain proper spine alignment or abdominal position in said punishment mode: or can be activated as long as the user pushes their abdomen beyond a minimum measurable distance and/or maintain a proper said posture in said encouragement mode;

wherein said abdominal muscles are caused to be exercised when said user-wearer is alerted and corrects said posture in said punishment mode or maintains said correct posture in said encouragement mode;

wherein said housing is structured and arranged to house said sensor, said memory unit, said processor of said alarm system to protect said sensor, said memory unit, and said processor from damage, said sensor in proximity to said torso of said user-wearer to sense relative position of said torso such that a proper alignment of a spinal column and said proper said posture is promoted;

wherein said sensor is in communication with said processor, said processor able to activate said music and alternately said vibrator;

wherein said power source provides power for said alarm system;

wherein said biofeedback belt system utilizes said biofeedback via said sensor to help/initiate decrease abdomen and stomach size as well as decrease an arch of a lower back of said user-wearer by inducing said vibration to indicate to said user-wearer of a poor said posture such that said posture is able to be corrected to said proper said posture; and wherein said music alone or in combination with said vibration mechanism, when played, indicates positive said biofeedback when said user-wearer corrects said posture such that a health and said proper said posture of said user-wearer is promoted.

2. The biofeedback belt system of claim 1 further comprising a kit including:

said biofeedback belt assembly; and a set of user instructions.

* * * * *